United States Patent
Desai

(10) Patent No.: US 8,192,075 B2
(45) Date of Patent: Jun. 5, 2012

(54) METHOD FOR PERFORMING ULTRASONIC TESTING

(75) Inventor: Anand Desai, Lewistown, PA (US)

(73) Assignee: GE Inspection Technologies, LP, Lewistown, PA (US)

( * ) Notice: Subject to any disclaimer, the term of this patent is extended or adjusted under 35 U.S.C. 154(b) by 958 days.

(21) Appl. No.: 12/194,000

(22) Filed: Aug. 19, 2008

(65) Prior Publication Data

US 2010/0046576 A1    Feb. 25, 2010

(51) Int. Cl.
*G01K 11/22* (2006.01)

(52) U.S. Cl. .......................... 374/119; 374/117

(58) Field of Classification Search .................. 374/100, 374/117, 119, 4–5, 118; 422/128; 264/40.1; 73/862.623
See application file for complete search history.

(56) References Cited

U.S. PATENT DOCUMENTS

| | | | |
|---|---|---|---|
| 4,246,784 A * | 1/1981 | Bowen | 374/117 |
| 4,772,131 A * | 9/1988 | Varela et al. | 374/119 |
| 5,040,415 A * | 8/1991 | Barkhoudarian | 73/198 |
| 5,062,086 A * | 10/1991 | Harlan et al. | 367/38 |
| 5,121,340 A * | 6/1992 | Campbell et al. | 702/54 |
| 6,512,586 B2 * | 1/2003 | Maris | 356/432 |
| 6,533,726 B1 * | 3/2003 | Lizzi et al. | 600/439 |
| 7,108,419 B2 * | 9/2006 | Harr | 374/121 |
| 7,404,671 B2 * | 7/2008 | Heyman et al. | 374/117 |
| 7,687,026 B2 * | 3/2010 | Laugharn et al. | 422/3 |
| 7,726,875 B2 * | 6/2010 | Yuhas | 374/119 |
| 7,811,525 B2 * | 10/2010 | Laugharn et al. | 422/128 |
| 2005/0281313 A1 * | 12/2005 | Qian et al. | 374/117 |

FOREIGN PATENT DOCUMENTS

DE    3316766 A1    1/1985

OTHER PUBLICATIONS

Fukuhara H et al: "Effect of Temperature on angle of refraction of sound waves produced by an angle probe" Transaction of National Research Institute for Metals Japan, vol. 21 No. 4, Nov. 1979, pp. 165-172 XP002546387.
PCT Search Report issued in connection with corresponding WO Patent Application No. US09/50462 filed on Jul. 14, 2009.

\* cited by examiner

*Primary Examiner* — Lisa Caputo
*Assistant Examiner* — Tania Courson
(74) *Attorney, Agent, or Firm* — GE Global Patent Operation; Mark A. Conklin

(57) ABSTRACT

Methods of performing ultrasonic testing are disclosed, comprising the step of determining a temperature gradient of an ultrasonic wedge. In one embodiment of the invention, the method further comprises the steps of determining a sound velocity gradient of the ultrasonic wedge to determine the time it takes for sound waves emanating from a plurality of ultrasonic transducer elements attached to the ultrasonic wedge to reach a point of interest within a test object, and firing each of the ultrasonic transducer elements in a timed sequence based on the times such that sound waves from each of the ultrasonic transducer elements reach the point of interest at the same time. In other embodiments of the invention, the total attenuation and acoustic impedance of a sound wave traveling through the ultrasonic wedge is determined to adjust the amplitude of the sound wave such that the sound wave has sufficient amplitude to perform the ultrasonic testing.

9 Claims, 7 Drawing Sheets

METHOD FOR PERFORMING ULTRASONIC TESTING

BACKGROUND OF THE INVENTION

This invention relates generally to nondestructive testing, and more particularly to a method for automatically adjusting ultrasonic testing systems to account for temperature variations in ultrasonic testing wedges.

Nondestructive testing devices can be used to inspect test objects to identify and analyze flaws and defects in the objects both during and after an inspection. Nondestructive testing allows an operator to maneuver a probe at or near the surface of the test object in order to perform testing of both the object surface and underlying structure. Nondestructive testing can be particularly useful in some industries, e.g., aerospace, power generation, and oil and gas recovery and refining, where object testing must take place without removal of the object from surrounding structures, and where hidden defects can be located that would otherwise not be identifiable through visual inspection.

One example of nondestructive testing is ultrasonic testing. When conducting ultrasonic testing, an ultrasonic pulse can be emitted from a probe and passed through a test object at the characteristic sound velocity of that particular material. The sound velocity of a given material depends mainly on the modulus of elasticity, temperature and density of the material. Application of an ultrasonic pulse to a test object causes an interaction between the ultrasonic pulse and the test object structure, with sound waves being reflected back to the probe. The corresponding evaluation of the signals received by the probe, namely the amplitude and time of flight of those signals, can allow conclusions to be drawn as to the internal quality of the test object without destroying it.

Generally, an ultrasonic testing system includes a probe for sending and receiving signals to and from a test object, a probe cable connecting the probe to an ultrasonic test unit, and a screen or monitor for viewing test results. The ultrasonic test unit can include power supply components, signal generation, amplification and processing electronics, and device controls used to operate the nondestructive testing device. Some ultrasonic test units can be connected to computers that control system operations, as well as test results processing and display. Electric pulses can be generated by a transmitter and can be fed to the probe where they can be transformed into ultrasonic pulses by ultrasonic transducers. Ultrasonic transducers incorporate piezoelectric ceramics which can be electrically connected to a pulsing-receiving unit in the form of an ultrasonic test unit. Portions of the surfaces of the piezoelectric ceramics can be metal coated, forming electrodes that can be connected to the ultrasonic test unit. During operation, an electrical waveform pulse is applied to the electrodes of the piezoelectric ceramic causing a mechanical change in ceramic dimension and generating an acoustic wave that can be transmitted through a material such as a metal or plastic to which the ultrasonic transducer is coupled. Conversely, when an acoustic wave reflected from the material under inspection contacts the surface of the piezoelectric ceramic, it generates a voltage difference across the electrodes that is detected as a receive signal by the ultrasonic test unit or other signal processing electronics.

The amplitude, timing and transmit sequence of the electrical waveform pulses applied by the pulsing unit can be determined by various control means incorporated into the ultrasonic test unit. The pulse is generally in the frequency range of about 0.5 MHz to about 25 MHz, so it is referred to as an ultrasonic wave from which the equipment derives its name. As the ultrasonic pulses pass through the object, various pulse reflections called echoes occur as the pulse interacts with internal structures within the test object and with the opposite side (backwall) of the test object. The echo signals can be displayed on the screen with echo amplitudes appearing as vertical traces and time of flight or distance as horizontal traces. By tracking the time difference between the transmission of the electrical pulse and the receipt of the electrical signal and measuring the amplitude of the received wave, various characteristics of the material can be determined. Thus, for example, ultrasonic testing can be used to determine material thickness or the presence and size of imperfections within a given test object.

Many ultrasonic transducers are phased arrays comprising single or multiple rows of electrically and acoustically independent or isolated transducer elements. A linear array of independent transducer elements can form what is referred to as a transducer pallet comprising a plurality of independent transducer elements. In these types of transducers, each transducer element may be a layered structure comprising a backing block, flexible printed circuit board ("flex circuit"), piezoelectric ceramic layer, and acoustic matching layer. This layered structure is often referred to as an acoustic stack. The various components of the acoustic stack can be bonded together using an adhesive material (e.g., epoxy) and high pressure in a lamination process. Typically, one or more flex circuits can be used to make electrical connections from the piezoelectric ceramic to the ultrasonic test unit, or to a bundle of coaxial cables that ultimately connect to the ultrasonic test unit or other signal processing electronics.

Ultrasonic testing systems typically employ a variety of probes depending on the test object, test object material composition, and environment in which the testing is being performed. For example, a straight-beam probe transmits and receives sound waves perpendicular to the surface of the object being tested. A straight-beam probe can be particularly useful when testing sheet metals, forgings and castings. In another example, a TR probe containing two elements in which the transmitter and receiver functions are separated from one another electrically and acoustically can be utilized. A TR probe can be particularly useful when inspecting thin test objects and taking wall thickness measurements. In yet another example, an angle-beam probe that transmits and receives sound waves at an angle to the material surface can be utilized. An angle-beam probe can be particularly useful when testing welds, sheet metals, tubes and forgings.

In some applications, e.g., when testing pipe welds, the probe can be mounted on a wedge that provides intermediary physical contact between the probe and the test object. Because the test object is typically of a different temperature than the wedge, the temperature of the wedge often changes as an inspection progresses. This temperature variation in the wedge introduces error into the ultrasonic testing process as the temperature variation of the wedge changes the velocity and attenuation of sound waves traveling through it. This, in turn, can result in transducer sound waves missing the intended point of interest and producing erroneous results. For example, in conducting a pipe weld inspection variations in wedge temperature may result in the ultrasonic pulse missing the known internal weld location and being directed to another location within the pipe.

Ultrasonic signals pass through the wedge and are refracted upon entering the test object. The refracted angle of the ultrasonic signal is dependent on Snell's Law: the sine of the refracted angle is directly proportional to the ratio of the speed of sound in the material used to construct the wedge divided by the speed of sound in the material of the test object.

Wedges can be made from any material that has an acoustic velocity different from that of the test object, but are typically manufactured from plastics such as plexi-glass or polystyrene material. The speed of sound in these materials varies widely with changes in temperature, thereby causing significant changes in refracted angles. In turn, changes in refracted angles of only a few degrees can direct the ultrasonic sound beam away from a point of interest, resulting in missed defects and erroneous results.

Compensating for thermal changes in the wedge is currently a manual process requiring calibration of the system based on measured environmental conditions. To calibrate the system, the ultrasonic testing system is removed from the test object and the wedge is brought to the same temperature as that of the test object, typically between −40 degrees C. to 100 degrees C. or higher. Once this has occurred, a calibration object with a known defect is attached and tested, and the sound angle of the probe adjusted until the defect appears at its known location. In order to perform such calibration, the ultrasonic testing system has to be removed from and re-attached to the test object each time the system is calibrated. This time and resource consuming calibration process has to be repeated after taking several measurements on the actual inspection target in order to ensure accurate results throughout the testing process.

Furthermore, the current calibration approach fails to take into account temperature gradients that exist within the wedge. As such the current calibration approach is based on an assumed constant temperature of the wedge and test object, the temperature of each being taken at a given point in time. In reality, the temperatures of both the wedge and test object change over time. In addition, the current approach assumes that the temperature of the wedge is consistent throughout the wedge material, when in reality it varies depending on what point on or within the wedge the temperature is taken. Therefore, despite the attempted calibration, subsequent testing is likely to have some degree of error and unreliability as either the angle or amplitude of the sound beam emitted by the transducers and introduced into the test object could be slightly askew, thereby missing or mischaracterizing defects within an object.

It would be advantageous to provide an apparatus and method for automatically adjusting transducer firing parameters to adjust for temperature gradients within the wedge, thereby reducing and/or eliminating the need for time consuming, resource intensive and unreliable manual calibration procedures.

BRIEF DESCRIPTION OF THE INVENTION

Methods of performing ultrasonic testing are disclosed, comprising the steps of: placing an ultrasonic wedge proximal to a test object; measuring the temperature of the test object; measuring the ambient temperature around the test object; and determining a temperature gradient of the ultrasonic wedge based at least in part on the ambient temperature and the temperature of the test object, wherein the temperature gradient provides the temperature at any point within the ultrasonic wedge.

In one embodiment of the invention, the method further comprises the steps of: determining a sound velocity gradient of the ultrasonic wedge based at least in part on the temperature gradient and the known velocity of sound for a given wedge material at a given temperature, wherein the sound velocity gradient provides the velocity of sound at any point within the ultrasonic wedge; determining the time it takes for sound waves emanating from a plurality of ultrasonic transducer elements attached to the ultrasonic wedge to reach a point of interest within the test object, wherein the times are based at least in part on the sound velocity gradient; and firing each of the ultrasonic transducer elements in a timed sequence based at least in part on the times such that sound waves from each of the ultrasonic transducer elements reach the point of interest at the same time.

In another embodiment of the invention, the method further comprises the steps of: determining an attenuation gradient of the ultrasonic wedge based at least in part on the temperature gradient and the known attenuation of sound for a given wedge material at a given temperature, wherein the attenuation gradient provides the attenuation of sound at any point within the ultrasonic wedge; determining the total attenuation of a sound wave emanating from an ultrasonic transducer element attached to the ultrasonic wedge as the sound wave travels through the ultrasonic wedge toward a point of interest within the test object and returns through the ultrasonic wedge to the ultrasonic transducer element, wherein the total attenuation is based at least in part on the attenuation gradient; and adjusting the amplitude of the sound wave emanating from the ultrasonic transducer element based at least in part on the total attenuation such that the sound wave has sufficient amplitude to perform the ultrasonic testing.

In yet another embodiment of the invention, the method further comprises the steps of: determining a sound velocity gradient of the ultrasonic wedge based at least in part on the temperature gradient and the known velocity of sound for a given wedge material at a given temperature, wherein the sound velocity gradient provides the velocity of sound at any point within the ultrasonic wedge; determining an acoustic impedance gradient of the ultrasonic wedge based at least in part on the sound velocity gradient and the known acoustic impedance of sound for a given wedge material at a given temperature, wherein the acoustic impedance gradient provides the acoustic impedance at any point within the ultrasonic wedge; determining the total acoustic impedance of a sound wave emanating from an ultrasonic transducer element attached to the ultrasonic wedge as the sound wave travels through the ultrasonic wedge toward a point of interest within the test object and returns through the ultrasonic wedge to the ultrasonic transducer element, wherein the total acoustic impedance is based at least in part on the acoustic impedance gradient; and adjusting the amplitude of the sound wave emanating from the ultrasonic transducer element based at least in part on the total acoustic impedance such that the sound wave has sufficient amplitude to perform the ultrasonic testing.

DETAILED DESCRIPTION OF THE INVENTION

Figure 1:
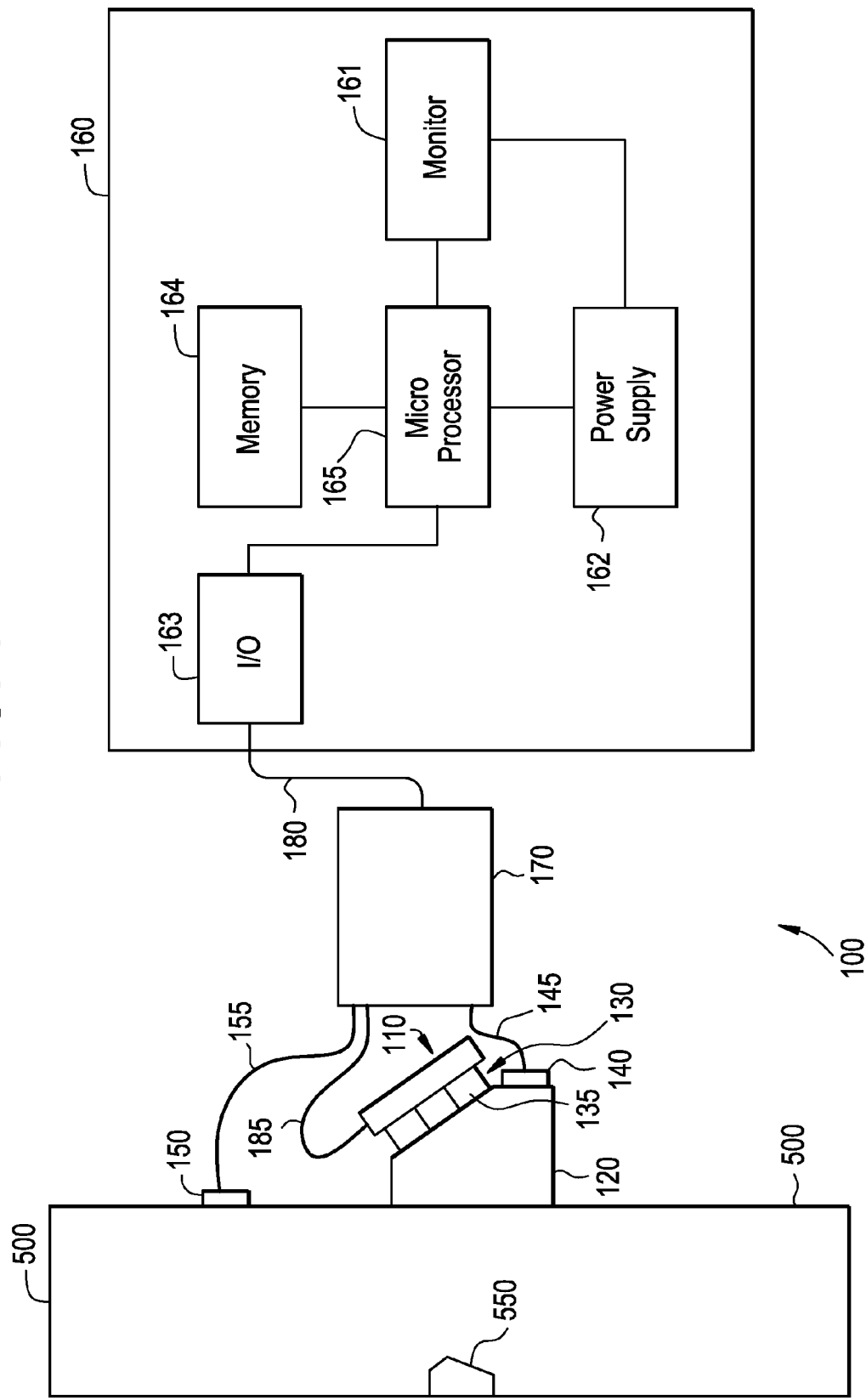
FIG. 1 is a block diagram of an ultrasound testing system.

FIG. 1 is a block diagram of an ultrasonic testing system 100 in combination with a test object 500 containing point of interest 550. In one embodiment, ultrasonic testing system 100 can comprise an ultrasonic wedge 120 that can be attached to a probe 110. Probe 110 can include various ultrasonic sound transmission and receiving components, such as an ultrasonic transducer array 130, and can provide a support structure for the transducer array to be attached to the ultrasonic wedge 120. The ultrasonic wedge 120 can be made from any material that has an acoustic velocity different from that of the test piece, but is typically made from plastics such as plexi-glass or a polystyrene material through which sound travels at a known velocity at a given temperature. Ultrasonic wedge 120 can provide a physical connection between ultrasonic transducer array 130 and the test object 500, and can work to reduce unintended noise from entering the ultrasonic testing process. Ultrasonic transducer array 130 can be comprised of one or more ultrasonic transducer elements 135. The amplitude and firing sequence of the individual ultrasonic transducer elements 135 can be controlled in order to adjust the angle and penetration strength of the ultrasonic sound beam that is sent into a test object 500. Probe cable 185 can connect the probe 110 to the ultrasonic testing unit 170. Ultrasonic testing unit 170 can comprise a power supply, and electrical signal generation and processing electronics. Ultrasonic pulser and receiver electronics can transmit and receive the ultrasonic signals. The received signals are typically processed through some type of analog to digital conversion, after which they are displayed as A-scans with amplitude on the y axis and time of flight on the x axis. These digital signals form the signature of a potential anomaly and are typically stored in memory and post processed to provide additional views for the operator to assist in determining if an anomaly is truly a defect or not. One or more microprocessors 165 can provide control over the entire process.

Ultrasonic testing unit 170 can be electrically connected to a computer 160 through an umbilical 180. The computer 160 can include a power supply 162, microprocessor 165 for running system software and controlling system operations, memory 164, an input/output controller for managing data being sent to and from, among other components, the ultrasonic testing unit 170, a keyboard (not shown), a joystick or mouse (not shown), a printer (not shown), and various other peripherals (not shown). Computer 160 can also comprise a monitor 161 for viewing system operations and inspection results.

An ambient temperature sensor 140 and a target temperature sensor 150 can be connected to the ultrasonic testing unit 170. The target temperature sensor 150 can be positioned such that it is in direct contact with the surface of the test object 500 under inspection, either as part of the ultrasonic wedge 120 or, as shown in FIG. 1, as a separate sensor mounted to the test object 500. The target temperature sensor 150 can be in electrical communication with ultrasonic testing unit 170 through sensor cable 155. The ambient temperature sensor 140, shown in FIG. 1 attached to an upper portion of the ultrasonic wedge 120, can be positioned in other embodiments anywhere such that it can accurately measure the temperature of the ambient air surrounding the test object 500 without that measurement being interfered with by a hot or cold test object 500 in close proximity. The ambient temperature sensor 140 can be in electrical communication with ultrasonic testing unit 170 through sensor cable 145. In one embodiment, commercially available temperature sensors such as thermocouples, thermistors, resistance temperature detectors (RTDs), or any combination of these elements can be used to take ambient and test object temperature measurements. Both the ambient temperature sensor 140 and target temperature sensor 150 can be in communication with the microprocessor 165 through electrical connections in the ultrasonic testing unit 170 and umbilical 180 to computer 160.

Figure 2:
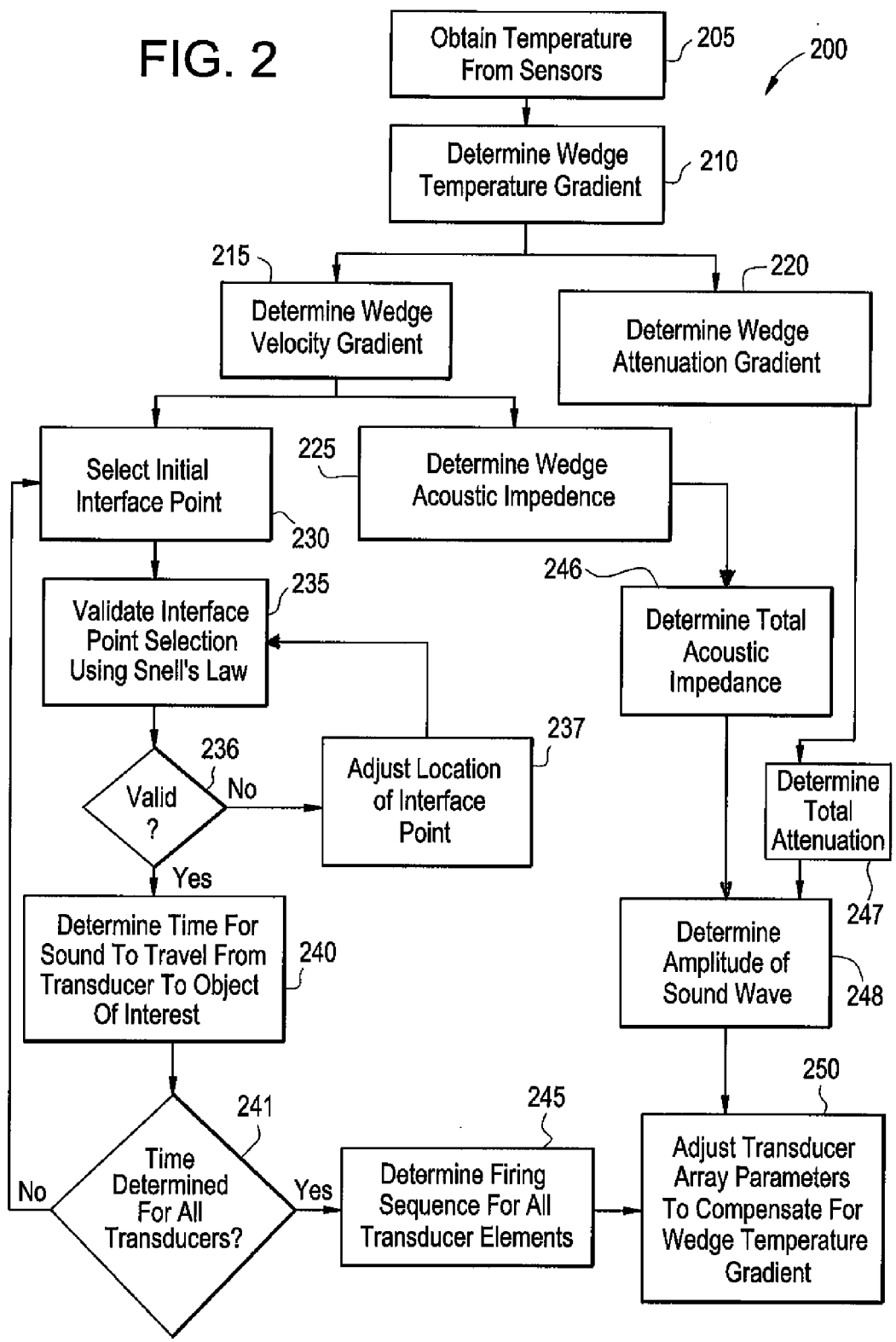
FIG. 2 is a block diagram of the steps that comprise an automated wedge temperature correction process.

FIG. 2 is a block diagram showing, in one embodiment, the sequence of steps that comprise an automated wedge temperature correction process 200 for the ultrasonic testing system 100 shown in FIG. 1. Each of the steps that comprise the automated wedge temperature correction process 200 can be controlled by software running on the microprocessor 165 within the ultrasonic testing system 100. The software can control the manipulation of system data and associated calculations, as well as the modification of system parameters to adjust the operation of the ultrasonic testing system 100, and, in particular, the firing sequence and amplitude of the ultrasonic transducer elements 135 within the ultrasonic transducer array 130.

Figure 3:
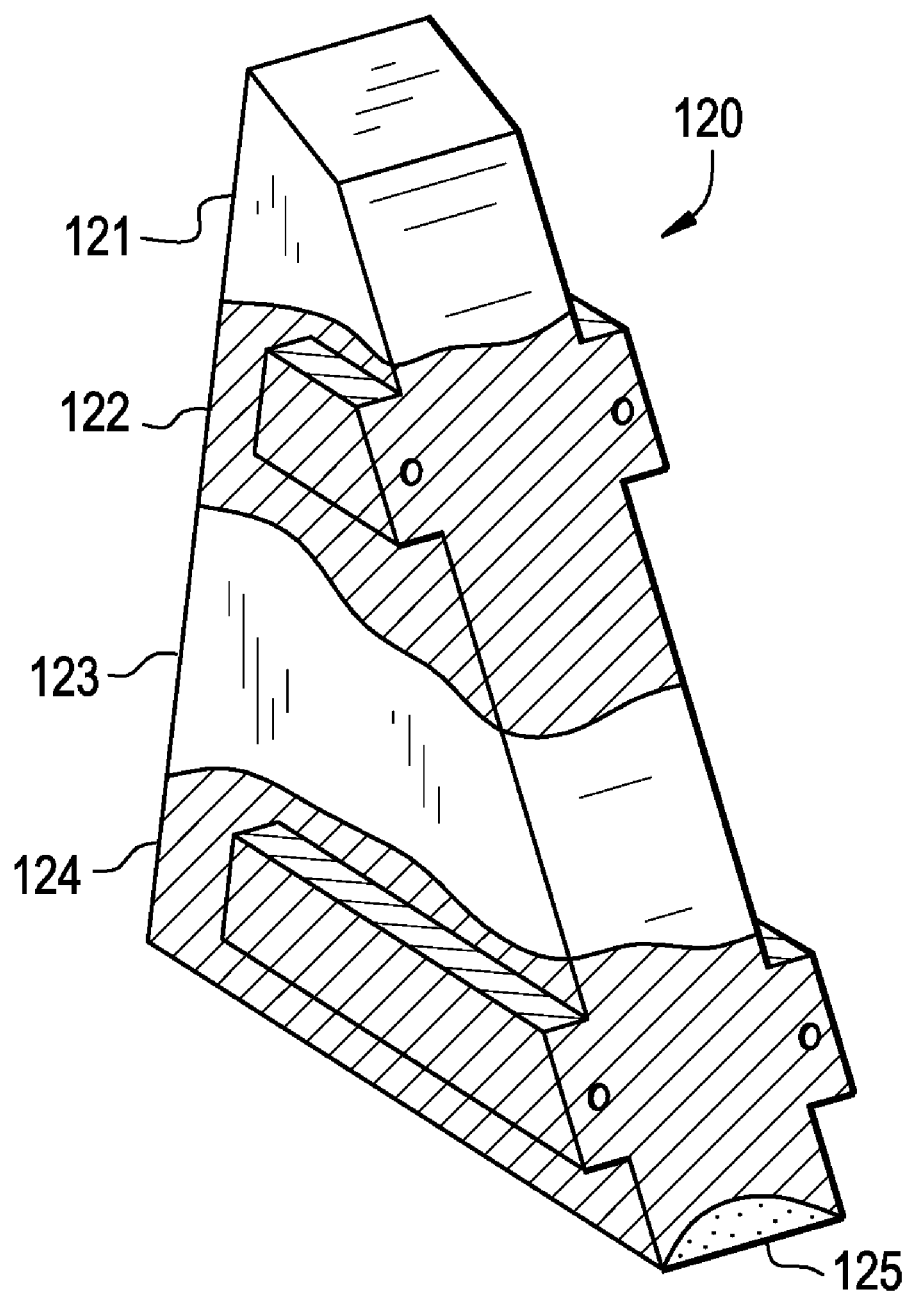
FIG. 3 is a perspective view of an exemplary ultrasonic wedge showing the temperature gradient within the ultrasonic wedge.

In Step 205, temperature readings from the ambient temperature sensor 140 and target temperature sensor 150 can be input to the microprocessor 165 where they can be used to determine the temperature gradient of the ultrasonic wedge 120 in Step 210. FIG. 3 shows an exemplary ultrasonic wedge 120 that has superimposed on it a numerical model of the temperature gradient within the ultrasonic wedge 120 when that ultrasonic wedge 120 is placed on top of a 100 degrees C. test object 500 for twenty minutes. For example, wedge layer 121, the portion of the ultrasonic wedge 120 furthest from test object 500, can be at a temperature of 30 degrees C., wedge layer 122 can be at a temperature of 50 degrees C., wedge layer 123 can be at a temperature of 70 degrees C., wedge layer 124 can be at a temperature of 90 degrees C., and wedge layer 125, the portion of ultrasonic wedge 120 closest to the test object 500, can be at a temperature of 100 degrees C. Using equation (1) below, the temperature gradient of the ultrasonic wedge 120 can be determined by calculating the temperature of the ultrasonic wedge 120 at any given location within the ultrasonic wedge 120:

$$\frac{T_n(x) - T_s}{T_\infty - T_s} = erf\left(\frac{x_n}{\sqrt{4\alpha_n(T)t}}\right) \text{ or } 1 - erfc\left(\frac{x_n}{\sqrt{4\alpha_n(T)t}}\right) \quad (1)$$

Where,
$T_n(x)$=Temperature at a location x along the length of the ultrasonic wedge in the $n^{th}$ layer
$T_s$=Test object temperature (at object surface)
$T_\infty$=Ambient temperature
erf=Error Function
erfc=Complementary Error Function
$x_n$=Location on the ultrasonic wedge height in the $n^{th}$ layer
t=Time
$\alpha_n(T)$=Thermal diffusivity in the $n^{th}$ layer which is a function of temperature In order to solve the formula and determine the temperature of the ultrasonic wedge 120 at any given location ($T_n(x)$), the actual temperature of the surface of the test object ($T_s$) can be taken from the target temperature sensor 150 and the ambient temperature of the test location ($T_\infty$) can be taken from the ambient temperature sensor 140. In addition to determining the ultrasonic wedge temperature at each location using the formula above, commercial software which uses finite element and finite volume schemes can be utilized.

Using the wedge temperature gradient determined in Step 210, Step 215 can then determine the sound velocity gradient in the ultrasonic wedge 120 as derived from the temperature-velocity relationship. Similarly, Step 220 can determine the sound attenuation gradient in the ultrasonic wedge 120 as derived from the temperature gradient, with the sound attenuation gradient providing the drop in amplitude of sound as it travels through a given layer of wedge material. The velocity and attenuation of sound as a function of temperature for any given wedge material can be obtained through experimental measurements, from literature, or through mathematical derivation. For example, equations for the velocity and attenuation of sound in an ultrasonic wedge material (e.g., natural ULTEM) are as shown below in equations (2) and (3) below:

$$V_n(T) = -72.551 T_n + 96026 \quad (2)$$

$$\text{Attn}_n(T) = -0.0281 T_n + 96026 \quad (3)$$

Figure 4:
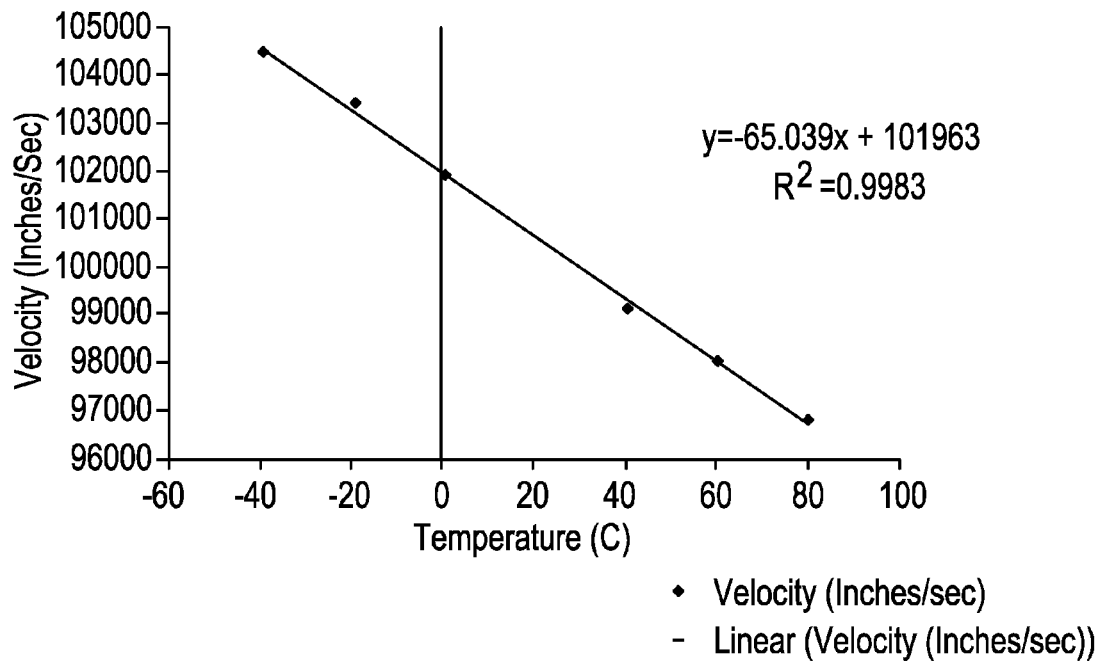
FIG. 4 is an exemplary graph showing the velocity of sound as a function of temperature in a given material.
Figure 5:
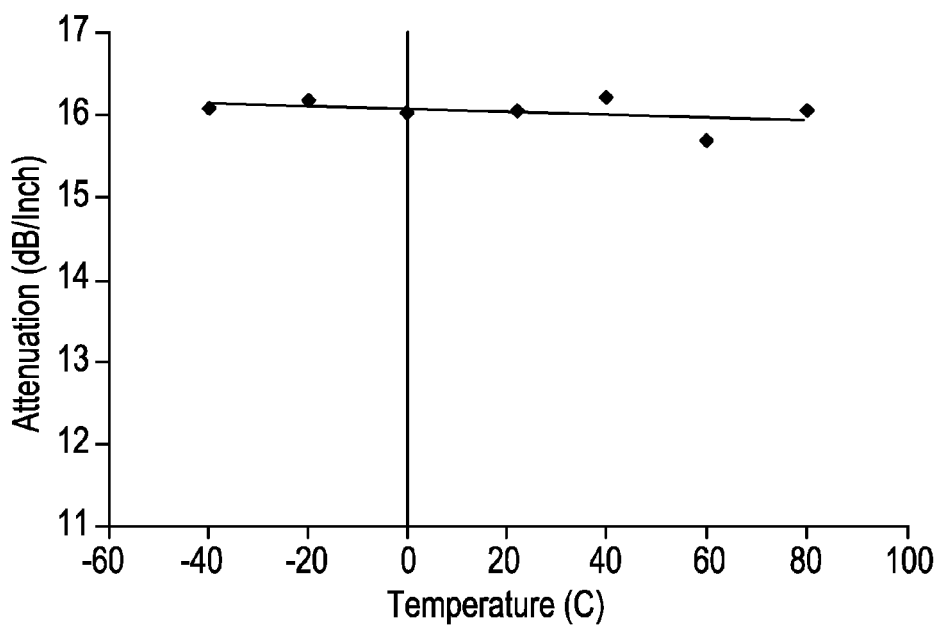
FIG. 5 is an exemplary graph showing the attenuation of sound as a function of temperature in a given material.

Where, $V_n(T)$=Velocity of sound in the ultrasonic wedge material in the $n^{th}$ layer as a function of temperature $\text{Attn}_n(T)$=Attenuation of sound in the ultrasonic wedge material in the $n^{th}$ layer as a function of temperature $T_n$=Temperature of the ultrasonic wedge material in the $n^{th}$ layer FIG. 4 shows an exemplary graph depicting the velocity of sound as a function of temperature in a given ultrasonic wedge material. Likewise, FIG. 5 shows an exemplary graph depicting the attenuation of sound as a function of temperature in a given ultrasonic wedge material.

By combining data from the wedge temperature gradient with data from the sound velocity gradient, the automated wedge temperature correction process 200 can predict changes in the velocity and direction of the ultrasonic beam with changes in the temperature of the ultrasonic wedge 120 at different locations on or within the ultrasonic wedge 120. The change in angle can be predicted by repeated use of Snell's Law, shown in equation (4) below:

$$\frac{\sin \alpha_{n-1}}{\sin \alpha_n} = \frac{v_{n-1}}{v_n} \quad (4)$$

Where,

Sin $\alpha_{n-1}$=Incident angle in layer n−1

Sin $\alpha_n$=Calculated incident angle in layer n $v_{n-1}$=Velocity of sound in layer n−1

$v_n$=Velocity of sound in layer n n=Layer anywhere between 2 and ∞

Figure 6:
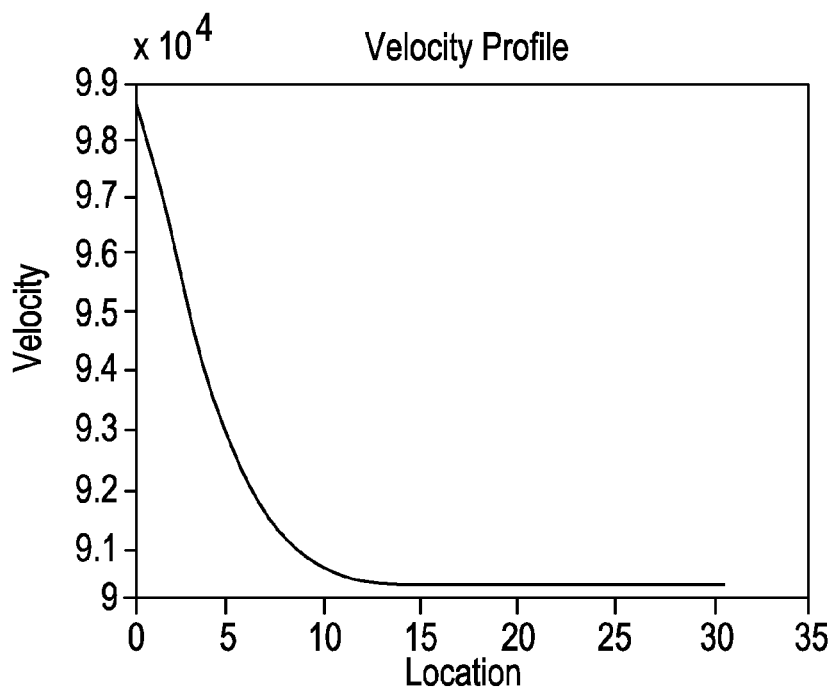
FIG. 6 is an exemplary graph showing the change in velocity of sound within an ultrasonic wedge as a result of the temperature gradient within the ultrasonic wedge.
Figure 7:
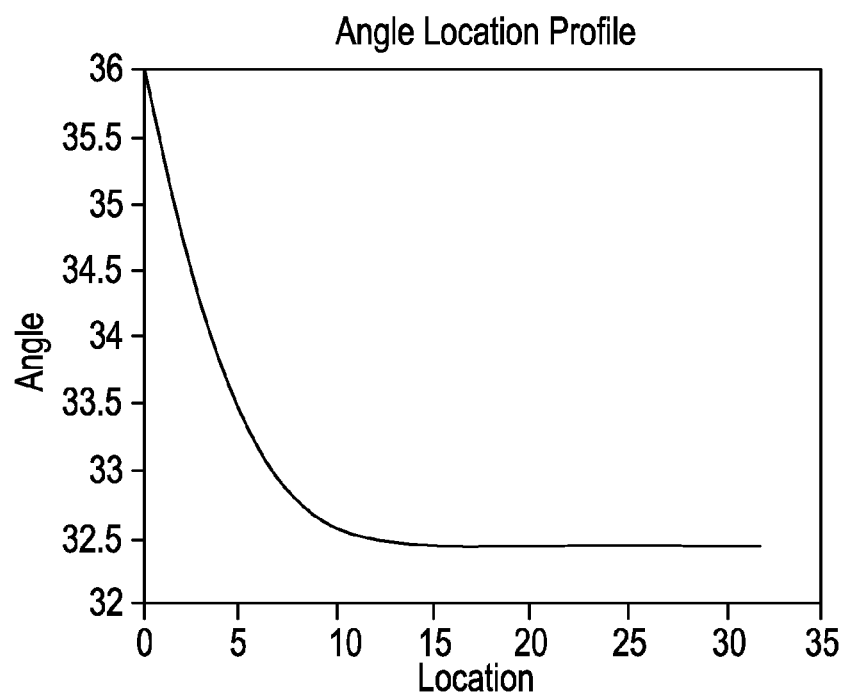
FIG. 7 is an exemplary graph showing the change in incident angle of sound inside an ultrasonic wedge as a result of the temperature gradient within the ultrasonic wedge.

Based on this information, data regarding the velocity of sound and the change in angle of the sound beam resulting from the temperature gradient of the ultrasonic wedge 120 can be obtained. FIG. 6 is an exemplary graph showing the change in velocity of sound at a given location within an ultrasonic wedge as a result of the temperature gradient within the ultrasonic wedge. FIG. 7 is an exemplary graph showing the change in incident angle of sound within an ultrasonic wedge as a result of the temperature gradient within the ultrasonic wedge.

Figure 8:
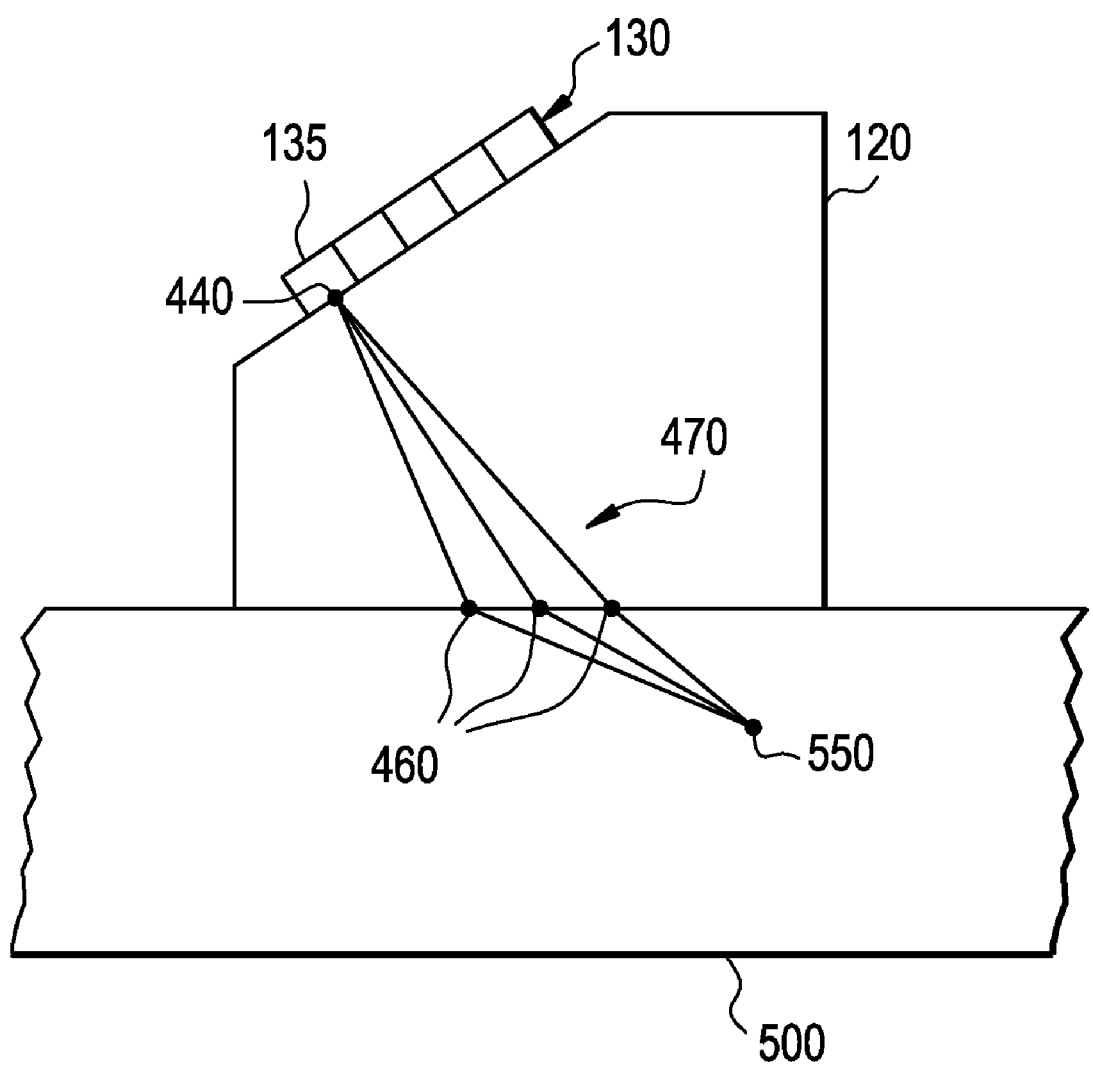
FIG. 8 is a block diagram of an ultrasonic transducer array, ultrasonic wedge, and test object combination with exemplary sound paths for one of the transducers.
Figure 9:
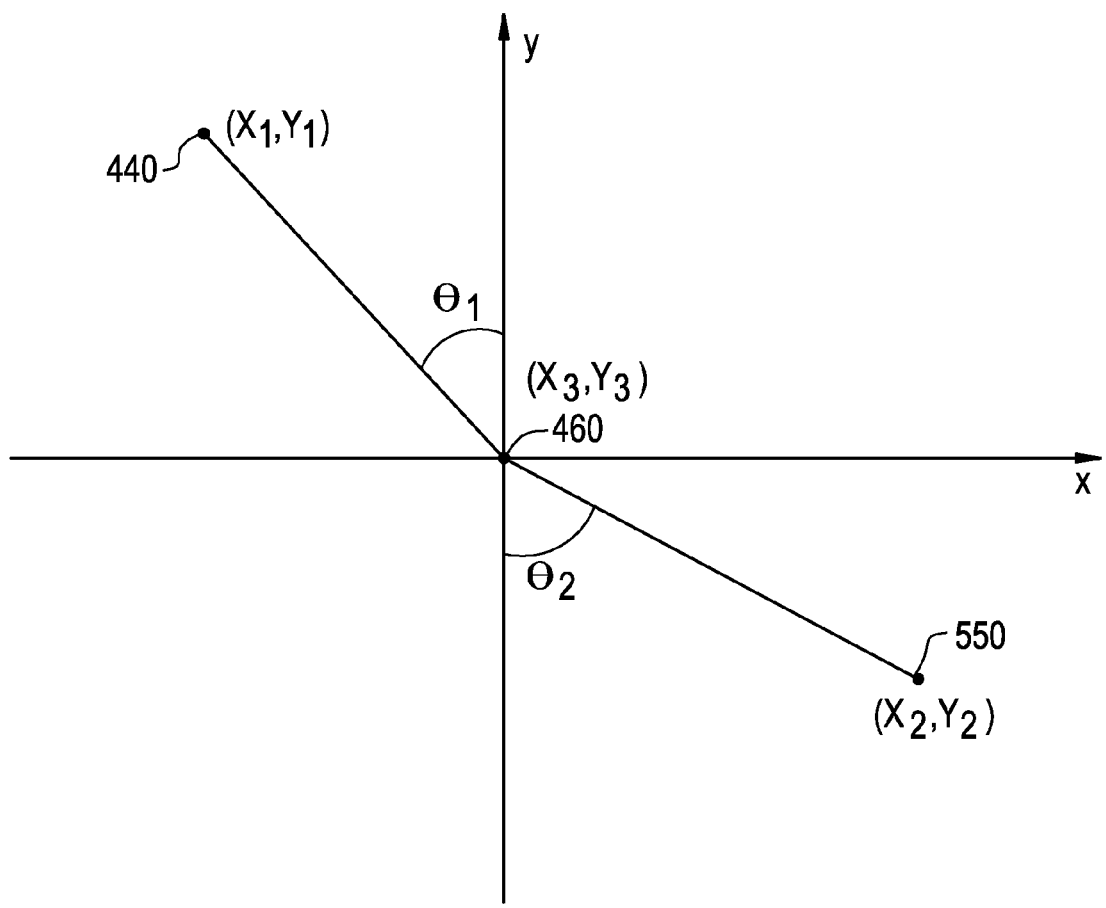
FIG. 9 is a planar x-y coordinate system with an exemplary sound path from an ultrasonic transducer mapped on it.

FIG. 8 shows a block diagram showing, in one embodiment, an ultrasonic transducer array 130 and ultrasonic wedge 120 combination mounted on a test object 500. FIG. 8 also shows exemplary sound paths 470 as they emanate from a center point 440 of one of the ultrasonic transducer elements 135, pass through the ultrasonic wedge 120, enter the test object 500 at an interface point 460, pass through test object 500, and arrive at the point of interest 550. FIG. 9 shows the path of one such exemplary sound path 470 mapped out on a planar x-y coordinate system centered on unknown interface point 460, designated as point ($x_3$, $y_3$), such that known center point 440, designated as point ($x_1$, $y_1$) is located at an angle $\theta_1$ from the vertical axis of coordinate system, and known point of interest 550, designated as point ($x_2$, $y_2$) is located at an angle $\theta_2$ from the horizontal axis of coordinate system. Using the known velocity value, $v_1$, of sound for any point in the ultrasonic wedge 120 determined in Step 215, as well as the velocity of sound in the test object 500, $v_2$, the automated wedge temperature correction process 200 can first determine the ratio of $v_1/v_2$, which according to Snell's Law as shown above in equation (4), must equal the ratio of $\sin \theta_1/\sin \theta_2$.

Knowing the locations of the center point 440 and point of interest 550, in Step 230 the automated wedge temperature correction process 200 can then select an initial interface point 460, designated ($x_3$, $y_3$), located on the x-y coordinate system, and can determine angles $\theta 1$ and $\theta_2$ by applying simple geometric calculations. In Step 235, the automated wedge temperature correction process 200 can then compare the ratio of $v_1/v_2$ to the ratio of $\sin \theta_1/\sin \theta_2$ for the calculated angles based on the selected interface point 460 location. If, at Step 236, the difference between $v_1/v_2$ to $\sin \theta_1/\sin \theta_2$ is within a predetermined tolerance, the system can use that interface point 460 location as determinative of the actual sound path, as that is the path that an ultrasonic sound pulse traveling from center point 440 to point of interest 550 will take in accordance with Snell's Law. If, however, the difference between the ratios exceeds a given tolerance, in Step 237 the interface point 460 can be incrementally moved in one direction or the other along the x-axis until the difference falls within the acceptable tolerance. In one embodiment, if the difference between the ratio of $v_1/v_2$ and the ratio of $\sin \theta_1/\sin \theta_2$ is greater than a given tolerance value the x coordinate of the interface point 460 is incremented, while if the difference is below a given tolerance value the x coordinate of the interface point 460 is reduced.

Once the coordinates of interface point 460 ($x_3$, $y_3$) are known along with the coordinates of center point 440 ($x_1$, $y_1$) and the point of interest 550 ($x_2$, $y_2$), the velocity gradient can be used in Step 240 to determine the time it takes a sound pulse to travel from the center point 440 to the point of interest 550. By repeating these Steps for each ultrasonic transducer element 135 in the ultrasonic transducer array 130 the microprocessor can, in Step 240, determine the time it takes for an ultrasonic pulse to reach the point of interest 550 from each of the ultrasonic transducer elements 135. In Step 241 the automated wedge temperature correction process 200 determines whether the pulse times are known for all of the ultrasonic transducer elements 135. If so, Step 245 can determine the overall firing sequence for the probe 110 such that the individual ultrasonic transducer elements 135 comprising the ultrasonic transducer array 130 can be timed in a way that ensures sound waves from each element will arrive at the point of interest 550 at the same time, thereby automatically correcting for the effects of temperature within the ultrasonic wedge 120. Step 250 then adjusts the firing parameters of each transducer element to conform to the firing sequence determined in Step 245. This allows for improved accuracy and reliability of the ultrasonic test, while at the same time reducing or eliminating altogether the need to manually calibrate the ultrasonic testing system 100.

Having determined the sound attenuation gradient in the ultrasonic wedge 120 at Step 220, the total attenuation of a sound wave emanating from an ultrasonic transducer element 135 as that sound wave travels through the ultrasonic wedge 120 toward a point of interest 550 within the test object 500 and returns through the ultrasonic wedge 120 to said ultrasonic transducer element 135 can be determined at Step 247, as shown in FIG. 2.

In addition, in Step 225, the velocity can be used to determine the acoustic impedance gradient of the ultrasonic wedge 120 using equation (5), shown below:

$$Z_n(T) = \rho_n(T) v_n(T) \tag{5}$$

Where,
$Z_n(T)$ = Acoustic impedance of the $n^{th}$ layer as a function of temperature
$\rho_n(T)$ = Density of the $n^{th}$ layer as a function of temperature
$v_n(T)$ = Velocity of sound in the $n^{th}$ layer as a function of temperature Having determined the acoustic impedance gradient in the ultrasonic wedge 120 at Step 225, the total acoustic impedance of a sound wave emanating from an ultrasonic transducer element 135 as the sound wave travels through the ultrasonic wedge 120 toward a point of interest 550 within the test object 500 and returns through the ultrasonic wedge 120 to said ultrasonic transducer element 135 can be determined at Step 246, as shown in FIG. 2.

Assuming the ultrasonic wedge 120 is comprised of small layers of materials with different acoustic impedance values correlating to the temperature variation inside the ultrasonic wedge 120, the acoustic impedance can be used to determine the transmission and reflection coefficient gradients of sound traveling through the ultrasonic wedge 120. The related equations for the transmission coefficient and reflection coefficient gradients are shown below in equations (6) and (7), respectively:

$$T_{n,n+1} = \frac{A_n}{A_{n+1}} = \frac{Z_n + Z_{in}^{(n)}}{Z_{n+1} + Z_{in}^{(n)}} \exp(i\phi_n) \tag{6}$$

$$V_{n,n+1} = \frac{B_{n+1}}{A_{n+1}} = \frac{Z_{in}^{(n)} - Z_{n+1}}{Z_{in}^{(n)} + Z_{n+1}} \tag{7}$$

Where, $$Z_{in}^{(n)} = \frac{Z_m^{(a-1)} - iZ_n \tan\phi_n}{Z_n - iZ_{in}^{(n-1)} \tan\phi_n} \cdot Z_n$$

$$\phi_n = \frac{2\pi f_n}{v_n} \cos(\alpha_n) d_n$$

$d_n$ = Thickness of the $n^{th}$ layer $v_n$ = Velocity of sound in the $n^{th}$ layer $f_n$ = Frequency of the probe $\alpha_n$ = Incident angle of the $n^{th}$ layer $\left| Z_{in}^{(n)} \right|$ = $n^{th}$ layer input impedance $$T_{n,n+1} = \left| \frac{A_n}{A_{n+1}} \right| =$$

Transmission coefficient between layers n and n+1; also represents the ratio of sound amplitudes between the two layers $$V_{n,n+1} = \left| \frac{B_{n+1}}{A_{n+1}} \right| =$$

Reflection coefficient of n+1$^{th}$ layer; also represents ratio of transmitted and reflected sound amplitudes for this layer The total attenuation of the sound wave determined at Step 247 and the total acoustic impedance determined at Step 246 of FIG. 2 can be used to better predict the echo, the signal that will be reflected and returned by the point of interest 550. Having a better understanding of the expected return signal allows an inspector to better understand and interpret test results as well as identify and differentiate between testing errors and actual defects. In addition, these determinations allow the automated wedge temperature correction process 200 to better determine the required transducer firing amplitude at Step 248 such that a sufficient echo signal is received. A sufficient echo signal, in turn, provides useable test results that exhibit a low signal to noise ratio to all ultrasonic testing to be accurately performed.

Therefore, using both the ambient and test object temperatures and known sound velocity characteristics for a given ultrasonic wedge material, the velocity gradient of sound in the ultrasonic wedge 120 can be obtained. The velocity gradient can then be used to predict the angle, attenuation, impedance and amplitude of a sound beam traveling through the material, which can then be used in Step 250 to predict and compensate for the effects of wedge temperature on the ultrasonic sound beam.

Although the embodiments of the invention shown and discussed herein for the most part perform the required calculations as a linear series of steps, it is clear that other embodiments can perform these steps either in different sequences or simultaneously to arrive at the same result.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of performing ultrasonic testing using ultrasonic transducer elements arranged in an array on an ultrasonic wedge proximate a test object, said method comprising the steps of:

receiving temperature readings from a target temperature sensor coupled to the test object and an ambient temperature sensor in position to measure the temperature of ambient air around the test object;

determining a temperature gradient of the ultrasonic wedge based at least in part on the temperature reading from the ambient temperature sensor and the temperature reading from the target temperature sensor of the test object, wherein the temperature gradient provides the temperature at any point within the ultrasonic wedge;

determining a sound velocity gradient of the ultrasonic wedge based at least in part on the temperature gradient and a known value for velocity of sound for a given wedge material at a given temperature, wherein the sound velocity gradient provides the velocity of sound at any point within the ultrasonic wedge;

determining the time it takes for sound waves emanating from the ultrasonic transducer elements attached to the ultrasonic wedge to reach a point of interest within the test object, wherein time is based at least in part on the sound velocity gradient; and firing each of the ultrasonic transducer elements in the array in a timed sequence, the timed sequence based at least in part on time so that sound waves from each of the ultrasonic transducer elements reach the point of interest at the same time.

2. The method of performing ultrasonic testing of claim 1, wherein said temperature gradient of said ultrasonic wedge is determined using the formula $$\frac{T_n(x) - T_s}{T_\infty - T_s} = \mathrm{erf}\left(\frac{x_n}{\sqrt{4\alpha_n(T)t}}\right) \text{ or } 1 - \mathrm{erfc}\left(\frac{x_n}{\sqrt{4\alpha_n(T)t}}\right),$$

wherein $T_n(x)$ is the temperature at a location x along the length of said ultrasonic wedge in the $n^{th}$ layer, $T_s$ is the test object temperature at the object surface, $T_\infty$, is the ambient temperature, erf is an error function, erfc is a complementary error function, $x_n$ is the location on said ultrasonic wedge height in the $n^{th}$ layer, t is time, and $\alpha_n(T)$ is the thermal diffusivity in the $n^{th}$ n layer as a function of temperature.

3. A method of performing ultrasonic testing using ultrasonic transducer elements arranged in an array on an ultrasonic wedge proximate a test object, said method comprising the steps of:

receiving temperature readings from a target temperature sensor coupled to the test object and an ambient temperature sensor in position to measure the temperature of ambient air around the test object;

determining a temperature gradient of the ultrasonic wedge based at least in part on the temperature reading from the ambient temperature sensor and the temperature reading from the target temperature sensor of the test object, wherein the temperature gradient provides the temperature at any point within the ultrasonic wedge;

determining an attenuation gradient of the ultrasonic wedge based at least in part on the temperature gradient and a known value for attenuation of sound for a given wedge material at a given temperature, wherein the attenuation gradient provides the attenuation of sound at any point within the ultrasonic wedge;

determining the total attenuation of a sound wave emanating from the ultrasonic transducer elements attached to the ultrasonic wedge as the sound wave travels through the ultrasonic wedge toward a point of interest within the test object and returns through the ultrasonic wedge to the ultrasonic transducer elements, wherein the total attenuation is based at least in part on the attenuation gradient; and adjusting the amplitude of the sound wave emanating from the ultrasonic transducer elements based at least in part on the total attenuation so the sound wave has sufficient amplitude to perform the ultrasonic testing.

4. A method of performing ultrasonic testing using ultrasonic transducer elements arranged in an array on an ultrasonic wedge proximate a test object, said method comprising the steps of:

receiving temperature readings from a target temperature sensor coupled to the test object and an ambient temperature sensor in position to measure the temperature of ambient air around the test object;

determining a temperature gradient of the ultrasonic wedge based at least in part on the temperatures reading from the ambient temperature sensor and the temperature reading from the target temperature sensor of the test object, wherein the temperature gradient provides the temperature at any point within the ultrasonic wedge;

determining a sound velocity gradient of the ultrasonic wedge based at least in part on the temperature gradient and a known value for velocity of sound for a given wedge material at a given temperature, wherein the sound velocity gradient provides the velocity of sound at any point within the ultrasonic wedge;

determining an acoustic impedance gradient of the ultrasonic wedge based at least in part on the sound velocity gradient and a known value for acoustic impedance of sound for a given wedge material at a given temperature, wherein the acoustic impedance gradient provides the acoustic impedance at any point within the ultrasonic wedge;

determining the total acoustic impedance of a sound wave emanating from the ultrasonic transducer elements attached to the ultrasonic wedge as the sound wave travels through the ultrasonic wedge toward a point of interest within the test object and returns through the ultrasonic wedge to the ultrasonic transducer elements, wherein the total acoustic impedance is based at least in part on the acoustic impedance gradient; and adjusting the amplitude of the sound wave emanating from the ultrasonic transducer elements based at least in part on the total acoustic impedance so the sound wave has sufficient amplitude to perform the ultrasonic testing.

5. The method of performing ultrasonic testing of claim 4, wherein said acoustic impedance gradient of said ultrasonic wedge is determined using the formula $Z_n(T)=\rho_n(T)v_n(T)$, wherein $Z_n(T)$ is the acoustic impedance of the $n^{th}$ layer, $\rho_n(T)$ is the density of the $n^{th}$ layer, and $v_n(T)$ is the velocity of sound in the $n^{th}$ layer.

6. The method of performing ultrasonic testing of claim 4, wherein the step of determining said total acoustic impedance comprises the step of determining the transmission coefficient gradient of said ultrasonic wedge based at least in part on said acoustic impedance gradient, wherein said transmission coefficient gradient provides the transmission coefficients between different layers within said ultrasonic wedge.

7. The method of performing ultrasonic testing of claim 6, wherein said transmission coefficient gradient of said ultrasonic wedge is determined using the formula $$T_{n,n+1} = \frac{A_n}{A_{n+1}} = \frac{Z_n + Z_{in}^{(n)}}{Z_{n+1} + Z_{in}^{(n)}} \exp(i\phi_n),$$

wherein $$Z_{in}^{(n)} = \frac{Z_{in}^{(a-1)} - iZ_n \tan\phi_n}{Z_n - iZ_{in}^{(n-1)} \tan\phi_n} \cdot Z_n, \phi_n = \frac{2\pi f_n}{v_n} \cos(\alpha_n) d_n,$$

$d_n$ is the thickness of the $n^{th}$ layer, $v_n$ is the velocity of sound in the $n^{th}$ layer, $f_n$ is the frequency of the probe, $\alpha_n$ is the incident angle of the $n^{th}$ layer, $Z_{in}^{(n)}$ is the $n^{th}$ layer input impedance, and $$T_{n,n+1} = \frac{A_n}{A_{n+1}}$$

is the ratio of sound amplitudes between layers n and n+1.

8. The method of performing ultrasonic testing of claim 4, wherein the step of determining said total acoustic impedance comprises the step of determining the reflection coefficient gradient of said ultrasonic wedge based at least in part on said acoustic impedance gradient, wherein said reflection coefficient gradient provides the reflection coefficients between different layers within said ultrasonic wedge.

9. The method of performing ultrasonic testing of claim 8, wherein said reflection coefficient gradient of said ultrasonic wedge is determined using the formula $$V_{n,n+1} = \frac{B_{n+1}}{A_{n+1}} = \frac{Z_{in}^{(n)} - Z_{n+1}}{Z_{in}^{(n)} + Z_{n+1}},$$

wherein $$Z_{in}^{(n)} = \frac{Z_{in}^{(n-1)} - iZ_n \tan\phi_n}{Z_n - iZ_{in}^{(n-1)} \tan\phi_n} \cdot Z_n, \quad \phi_n = \frac{2\pi f_n}{v_n} \cos(\alpha_n) d_n,$$

$d_n$ is the thickness of the $n^{th}$ layer, $v_n$ is the velocity of sound in the $n^{th}$ layer, $f_n$ is the frequency of the probe, $\alpha_n$ is the incident angle of the $n^{th}$ layer, $Z_{in}^{(n)}$ is the $n^{th}$ layer input impedance, and $$V_{n,n+1} = \frac{B_{n+1}}{A_{n+1}}$$

is the ratio of transmitted and reflected sound amplitudes between layers n and n+1.

* * * * *